United States Patent [19]

Boretos et al.

[11] 4,265,694
[45] May 5, 1981

[54] METHOD OF MAKING UNITIZED THREE LEAFLET HEART VALVE

[75] Inventors: John W. Boretos, Rockville, Md.; Norio Iriguchi, Fuji, Japan

[73] Assignee: The United States of America as represented by the Department of Health, Education and Welfare, Washington, D.C.

[21] Appl. No.: 114,298

[22] Filed: Jan. 22, 1980

Related U.S. Application Data

[62] Division of Ser. No. 969,571, Dec. 14, 1978, Pat. No. 4,222,126.

[51] Int. Cl.³ .............................................. B29C 27/00
[52] U.S. Cl. ........................................ 156/242; 3/1.5; 156/245
[58] Field of Search ............... 156/242, 245, 293, 294; 264/328; 3/1.5

[56] References Cited

U.S. PATENT DOCUMENTS

| | | | |
|---|---|---|---|
| 2,662,724 | 12/1953 | Kravagna | 3/1.5 |
| 3,320,972 | 5/1967 | Hugh et al. | 3/1.5 |
| 3,445,916 | 5/1969 | Schulte | 3/1.5 |
| 3,548,417 | 12/1970 | Kischer | 3/1.5 |
| 3,744,062 | 7/1973 | Parsonnet | 3/1.5 |
| 3,755,823 | 9/1973 | Hancock | 3/1.5 |
| 3,940,802 | 3/1976 | Sako et al. | 3/1.5 |
| 4,172,295 | 10/1979 | Batten | 3/1.5 |

OTHER PUBLICATIONS

"Segmented Polyurethane: A Polyether Polymer", John W. Boretos et al., Journal of Biomedical Materials Research, vol. 2, No. 1, Mar. 1968, pp. 121–130.

Primary Examiner—Caleb Weston
Attorney, Agent, or Firm—Browdy and Neimark

[57] ABSTRACT

An artificial heart valve comprising a semi-rigid framework having three projecting symmetrical struts and open axially therethrough, as well as a polyurethane elastomeric membrane attached to the struts and constituting three leaflets, is formed by molding the framework, including the base and strut, using polyurethane resin; forming the elastomeric membrane, of polyurethane resin which is thin relative to the framework, and forming a thickened commissure along the leading edge of the membrane as well as reinforcing lines radiating from its base; then joining the framework with the elastomeric membrane using an adhesive cement so as to permanently bond the membrane to the framework.

9 Claims, 6 Drawing Figures

METHOD OF MAKING UNITIZED THREE LEAFLET HEART VALVE

This is a division of application Ser. No. 969,571 filed Dec. 14, 1978, now U.S. Pat. No. 4,222,126.

FIELD OF THE INVENTION

The invention relates to prosthetic devices, and, in particular, a valve useful in replacing natural heart valves.

BACKGROUND OF THE INVENTION

Currently there are various types of artificial heart valves which have been proposed for clinical use. They include: (1) those made of a rigid metal frame with a central occluder which functions as a check valve with each beat of the heart, (2) tissue valves made from an animal's (pig) heart valve that is stretched and sewn over a rigid metal framework to provide central flow of blood, and (3) tri-leaflet valves of limited longevity and reliability. Such valves have never been clinically acceptable.

Central occluder valves consist, typically, of "ball-in-cage" or low-profile "disc-in-cage" designs utilizing plastic, silicone rubber, carbon or metal occluders. The rubber occluders suffer from two major shortcomings: (a) they are subject to "lipid" adsorption from the blood stream with concomitant changes in dimensions and physical integrity; splitting, tearing, and clotting result (see:

Bonnabeau, R. C. Jr., and Lillehei, C. W.: "Mechanical ball failure in Starr-Edwards Prosthetic Valves", *J. Thorac. Cardiovas. Surg.* 56: 258, 1968;

Hylen, J. C.: "Durability of Prosthetic Heart Valves", *Am. Heart J.* 81: 299, 1971;

Hylen, J. C., Hodam, R. P. and Kloster, F. E.: "Changes in the Durability of Silicone Rubber in Ball-Valve Prostheses", *Annals Thorac. Surg.* 13: 324, 1972;

Aston, S. J. and Mulder, D. G.: "Cardiac Valve Replacement, A Seven-Year Follow-up", *J. Thorac. Cardiovas. Surg.* 61: 547, 1971;

Starr, A., Pierie, W. R., Raible, D. A., Edwards, M. L., Siposs, G. C., and Hancock, W. D.: "Cardiac Valve Replacement, Experience With the Durability of Silicone Rubber", *Suppl. I to Circulation,* 33, 34, April 1966) and (b) they possess a low order of wear resistance (see Boretos, J. W., Detmer, D. E. and Donachy, J. H. "Segmented Polyurethane: A polyether Polymer, II, Two Years Experience", *J. Biomed. Mater. Res.* 5: 373, 1971).

Clinical evidence with the "low profile" design exemplifies this characteristic, (Detmer, D. E.; McIntosh, C. L.; Boretos, J. W.; Braunwald, N. S.: "Polypropylene Poppets for Low-Profile Prosthetic Heart Valve", *Annals Thorac. Surg.* 13: 122, 1972).

The metal and carbon occluders are: (a) abrasive to cloth covered struts causing fragmentation of the cloth with ensuing emboli, (Detmer, D. E. and Braunwald, N. S.: "The Metal Poppet and the Rigid Prosthetic Valve", *J. Thorac. Cardiovas. Surg.* 61: 175 1971;

Ablaza, S. G. G., Blanco, G., Javan, M. B., Maranhao, V. and Goldberg, H. "Cloth Cover Wear of the Struts of the Starr-Edwards Aortic Valve Prosthesis", *J. Thorac, Cardiovas. Surg.* 61: 316, 1971;

Thomas, C. S., Killen, D. A., Alford, W. C., Burrus, G. R. and Stoney, W. S.: "Cloth Disruption in the Starr-Edwards Composite Mitral Valve Prosthesis", *Annals Thorac. Surg.* 15: 434, 1973).

Cloth covering has been shown to minimize thrombus formation on metal frames and is generally considered necessary for these designs, (Detmer, D. E. and Braunwald, N. S. "The Metal Poppet and the Rigid Prosthetic Valve", *J. Thorac. Cardiovas. Surg.* 61: 175, 1971;

Ablaza, S. G. G., Blanco, G., Javan, B. B., Maranhao, V. and Goldberg, H. "Cloth Cover Wear of the Struts of the Starr-Edwards Aortic Valve Prosthesis", *J. Thorac. Cardiovas. Surg.* 61: 316, 1971 ).

However, paravalvular leaks caused by cloth wear on the valve seats are responsible for high blood hemolysis, (Thomas, C. S., Killen, D. A., Alford, W. C., Burrus, G. R. and Stoney, W.: "Cloth Disruption in the Starr-Edwards Composite Mitral Valve Prosthesis", *Annals Thorac. Surg.* 15: 434, 1973).

The metal and carbon occulders are also: (b) abrasive to bare metal valve surfaces, especially for metal to metal contact, and (c) hard and they accordingly generate a "clicking" sound with each cycle. This noise and its associated anticipation is highly distressing to patients. In addition, in metal and carbon occluders (d) the central flow of blood is blocked by the presence of the occluder, reducing the potential volume output, increasing resistance to flow, and causing turbulence of flow which is believed to add to the incidence of thrombo embolism.

Tissue valves are generally made by sewing excised pig valves over a rigid framework. These have the following disadvantages: (a) Tissue valves individually variable due to the fact that they are extracted from a living animal and subject to extremes of physical and physiological differences which have occured during growth of the animal (b) There is no absolute way of testing individual valves for strength and durability prior to use. (c) Fixation techniques must be used to preserve tissue valves after extraction and during fabrication and storage and bacterial invasion has been difficult to control. Absolute sterility is difficult to assure, and patients occasionally become physically distressed due to bacterial endocarditis following surgical placement of a tissue valve. (d) Long-term implants have shown evidence of calcium deposits generated on the surface of the leaflets in some cases rendering them stiff and non-functional. (e) Tissue valves are not suitable for use in artificial heart assist devices where assembly, storage, and sterilization of the device must be done well in advance of surgery and under conventional sterilization techniques which would greatly impair or destroy living tissues.

Over the past 20 years a number of trileaflet valves has been constructed. Various materials and combinations of materials such as epoxies, silicones, Teflon, Dacron, and polyester polyurethanes have been used. For example, the patent to Sako et al, U.S. Pat. No. 3,940,802 discloses a non-toxic compound for use in heart valves, comprising 100 parts by weight PVC and 50–100 parts by weight of polyurethane. Generally these valves have been clinically unsuccessful for the following reasons: Sinicone-Dacron polyester valves of a trileaflet configuration require the cusps to be made thick, relative to normal tissue valves, to give them strength and shape. Unreinforced silicone rubber is too weak to be used alone. Unfortunately, the Dacron reinforcement prevents efficient opening and closing of the valve and significantly reduces the flexural fatigue resistance of the silicone. Fracture of the fibers results in premature failure. Poor performance in the form of regurgitation of blood is a common problem with such stiff valves.

Uncoated fabric valves of Dacron or Teflon have proven unsatisfactory because of the loss of function due to heavy fiberous tissue ingrowth which impairs opening and closing. Teflon has been shown to rapidly fragment due to fatigue failure.

Polyurethane tri-leaflet valves attempted in the past suffer from the following defects: (a) Leaflets detach from their mounting frames when assembled from individual leaflets. (b) Leaflets flex-fatigue at the mounting frame when the frame is rigid, concentrating the flexural strain pattern at a point along the rigid-flexible junction. (c) The thin leaflet construction, when unreinforced, has a propensity to tear along its commissure line; reinforced materials are too stiff to function (d) Previous polyurethane leaflet valves were constructed of a hydrolytically unstable polyester polyurethane which rapidly degrades in the blood stream causing premature failure. (e) Thrombi generated on the surface were common occurrences with earlier designs using polyester polyurethanes. (f) Use of dissimilar materials can induce adverse reactions in designs where polyurethane leaflets are attached to an epoxy frame. In such cases, residual amines from the epoxy can migrate into the polyurethane causing degradation of physical properties and adverse surface characteristics may develop which can stimulate an inflamatory, toxic, or otherwise incompatible condition.

The patents to Hancock, U.S. Pat. No. 3,755,823; Parsonnet, U.S. Pat. No. 3,744,062, and Kischer, U.S. Pat. No. 3,548,417 are examples of prior art heart valves which suffer from one or more of the defects noted above.

SUMMARY OF THE INVENTION

It is, accordingly, an object of the present invention to overcome the deficiencies of the prior art, such as mentioned above.

It is another object to provide for improved heart function for hearts having diseased or otherwise defective valves.

It is a further object of the present invention to provide an artificial heart valve made of polyurethane, having three projecting struts integral with an elastomeric membrane whose contours make up the three leaflets of the valve.

It is a further object of the present invention to provide an artificial heart valve made of polyurethane, preferably polyether polyurethane, which has outstanding physical strength and durability, physiological acceptability and can be easily manufactured.

If the heart should fail during surgery and not respond to emergency measures such as electrical stimulation, drugs, or intravascular balloon techniques, the surgeon may elect to sustain life with an artificial assist pump to maintain function until normal cardiac output is restored. Although assist pumps are still in the developmental stage, some designs have been successful for periods of several weeks in experimental animals and to a limited extent clinically. These devices incorporate conventional artificial heart valves for controlling diastolic/systolic sequelae. The present tri-leaflet valve can be used in these devices and is capable of providing unobstructed flow, minimal turbulence, efficient cyclic performance, and endurance.

The device which achieves these objectives uses a "unitized" trileaflet design, comprising a semi-rigid polyurethane framework whose three projecting struts are an integral part of and support, a one-piece, highly flexible, elastomeric membrane whose contours make up the three leaflets of the valve. The leading edges of the leaflets, which go together to form the commissure line, are reinforced with a narrow band of the same elastomer which makes up the membrane leaflets and is an integral part of the membrane. Further reinforcement by means of radiating lines projecting from the frame into the leaflet area combine with a smooth and filleted transition line between the two to enhance strength and durability without appreciably adding bulk or stiffness. These lines simulate collagen formation as it appears in natural leaflets. A compliant base which is a permanent part of the valve body provides for attachment of the valve to the tissues of the heart.

The invention offers mechanical reliability in the form of outstanding physical strength and durability, improved functional performance, physiological acceptability, and practical manufacturing capabilities. The combination of these attributes offers a degree of sophistication and utility not previously available in artificial heart valves.

The unitized tri-leaflet construction offers mechanical reliability in the following manner:

(a) leaflets are not readily torn or fatigued due to flexing during use;

(b) the valve does not require the use of cloth, flocking or other textile forms for strength;

(c) the possibility of abrasion due to bearing or rubbing surfaces is avoided;

(d) leaflets are of a thin membrane structure and biaxially oriented for unusually high strength and durability while, at the same time, maintaining a gossimer-like characteristic for ease of operation at normal blood pressures;

(e) the entire structure is made from one material, such as polyether polyurethane, thereby precluding the possibility of interactions between dissimilar materials;

(f) all three leaflets are basically one piece and cannot separate from each other or the frame to which they are attached;

(g) the edges or lips of the leaflets are heavier than the main body of the leaflets and form a tight and durable seal at the commissure line of the valve with each closing cycle whereby flexing of the valve struts accomodates the complete and natural closing configuration and minimizes stress along the leaflet edges;

(h) the junction between the leaflets and the frame is a smooth transition to obviate stress concentration and distribute it throughout;

(i) radiating lines from the above junction add additional reinforcement for flexural strength and stress distribution without increasing bulk or stiffness;

(j) valves of this design are not subject to being misshapened due to misalignment when sutured in place of the natural valve;

(k) the base of the valve cannot be detached and is a permanent part of the valve;

(l) the base can be of a rigid polurethane flange shape or a flexible porous or foam polyurethane construction or a combination of both, and can be covered with cloth or incorporate cloth padding to lend strength and ease of insertion for permanent fixation to the living tissues, heart wall or vessel.

The unitized tri-leaflet construction offers improved functional performance by:

(a) allowing for uninterrupted central laminar flow of blood similar to that of the natural valve;

(b) providing the leaflets with a gossimer nature that offers very little resistance;

(c) providing rapid opening and closing;

(d) providing complete, unobstructed opening and complete non-regurgitant closing;

(e) simulating the natural valve in size and shape without blocking adjacent blood vessel orifices when implanted;

(f) providing struts that are rigid enough not to allow the leaflets to invert upon themselves even though a very low profile is used.

The unitized tri-leaflet construction offers physiological acceptability by:

(a) providing surfaces which are compatible with the blood and of a polyether urethane type;

(b) providing surfaces which are free from tissue-ingrowth of fibrous encapsulation;

(c) providing a valve which is hydrolytically and enzymatically stable and does not degrade in the blood stream over extended periods of time;

(d) providing surfaces which are smooth and clean and do not encourage calcium deposits on their surfaces;

(e) obviating the formation of emboli to the brain or lungs by excluding release of fragments of textile materials from flexing areas of the valve;

(f) using biocompatible polyurethanes of a polyether type which are free from absorption of body fluids which could alter them physically or chemically;

(g) providing all surfaces that can be readily treated with anti-coagulants or other blood compatible materials.

The unitized tri-leaflet design offers practical manufacturing capabilities by being:

(a) readily sterilized by conventional methods;

(b) manufactured in large numbers. Its structure can be varied in size according to patient needs and does not rely upon living donors;

(c) constructed entirely from man-made materials and as such is suiable for use in artificial heart assist devices which must undergo conditions of complex assembly, sterilization and storage;

(d) industrially producible to a high degree of duplication and reliability.

Polyether polyurethanes, from which the valve can be made, have shown themselves to have outstanding biocompatibility, strength, flex-life, and versatility.

For a better understanding of the invention, a possible embodiment thereof will now be described with reference to the attached drawing, it being understood that this embodiment is exemplary and not limitative.

DETAILED DESCRIPTION OF THE PREFERRED EMBODIMENT

Figure 1:
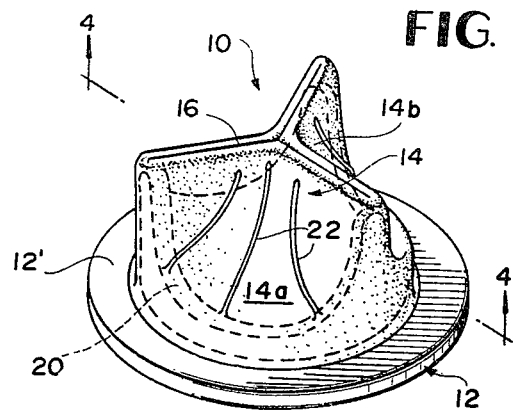
FIG. 1 is a perspective view of an embodiment of the heart valve of the present invention, in the diastolic mode.
Figure 3:
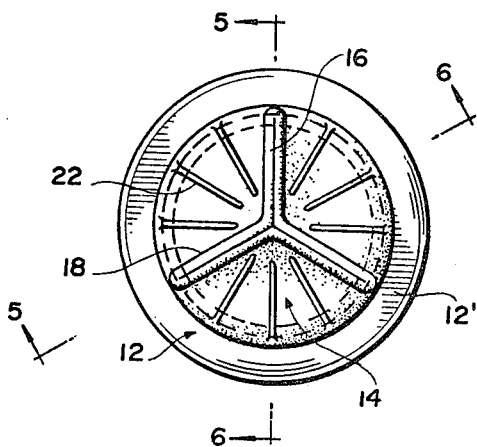
FIG. 3 is a top view of the heart valve of the embodiment of FIG. 1.

A tri-leaflet heart valve 10 as shown in FIG. 1 comprises a rigid polyurethane frame 12 covered with a one-piece membrane 14 that forms the three polyurethane leaflets 14a, 14b, and 14c and bonded in place to the frame 12 to form a single integral unit. The material of construction can be any polyether polyurethane such as Biomer ® (Ethicon, Inc.) or Pellethane ® (Upjohn Co.) or a combination of these and others that have biocompatibility and strength.

The frame 12 is of a construction which serves to anchor the leaflets and maintain proper alignment after implantation. The frame 12 consists of two distinct but inseparable areas, namely a base ring 12' which establishes the orifice size, and the three struts 12a, 12b and 12c which support the leaflets and distribute the strain of cyclic flexing. The height of the struts 12a, 12b and 12c are important, as when the struts are too short (less than $\frac{1}{4}$ inch), the strain force in the leaflets 14a, 14b, and 14c caused by the blood pressure against them becomes seriously high. Sustained operation under these conditions would result in rapid fatigue failure of the leaflets. To avoid this problem, the height of the leaflets 14a, 14b and 14c can exceed the height of the struts. When the struts 12a, 12b and 12c are too long (more $\frac{3}{4}$ inch), the bending force against the struts, caused by the pressure of the blood against the leaflets, concentrates the strain at a point within the struts leading to fatigue. Thus, the most suitable and preferred length of the struts 12a, 12b and 12c is $\frac{1}{2}$ to $\frac{3}{4}$ inch and most particularly $\frac{1}{2}$ inch. With this construction, the stress within the struts and the leaflets is reduced to an optimum level.

Figure 2:
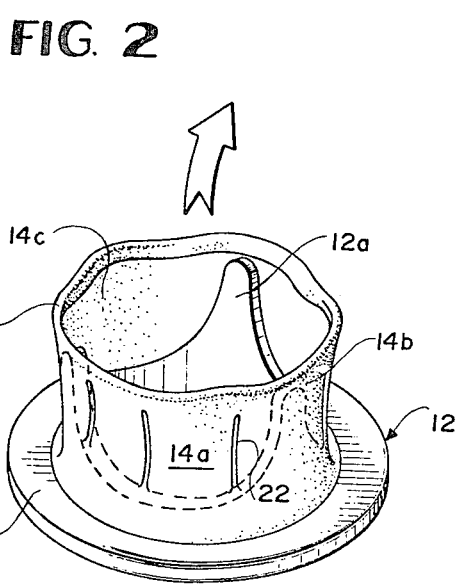
FIG. 2 is a perspective view of the embodiment of FIG. 1 in the open position during systole.
Figure 4:
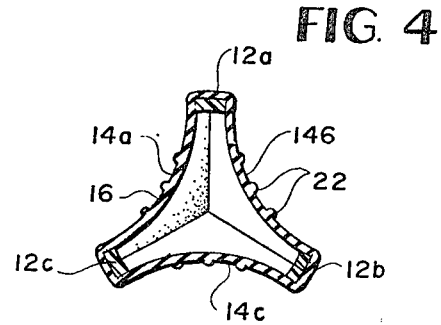
FIG. 4 is a horizontal sectional view taken along line 4—4 of FIG. 1.
Figure 5:
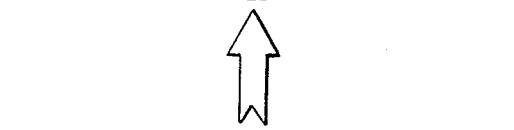
FIGS. 5 and 6 are vertical sectional views along lines 5—5 and 6—6, respectively, of FIG. 3.
Figure 6:
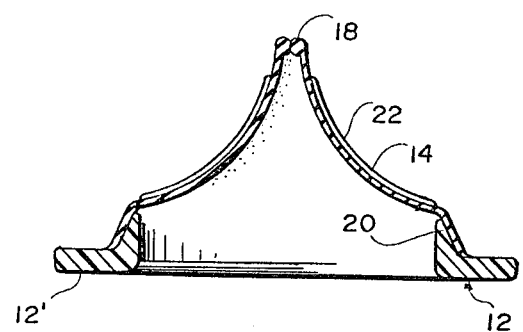

The construction of the leaflets 14a, 14b and 14c are such that they function similarly to that of the natural heart valve even though they are partially supported by the frame 12. In the open position, i.e. when the blood is flowing freely throughout the central opening formed by the leaflets as shown in FIG. 2, the orifice consists of a complete and uninterrupted circle equal to or larger than the inside diameter of the base ring 12', thereby providing unrestrained and laminar fluid flow. This flow pattern does much to obviate artificially induced thrombii that could be produced due to random flow patterns, turbulence of back-flow. In the closed position, i.e. when the blood is checked from flowing through the heart valve, as shown in FIG. 1, the leaflets abut each other at the commissure line 16 insuring complete closure and competency. Strain levels along the commissure line 16 are reduced to a minimum by the distribution of strain to the frame struts 12a, 12b and 12c and through the body of the device.

Further, the membrane 14 is provided with a thickened lip 18 which forms the free ends of the leaflets 14a, 14b, and 14c which thickened lip 18 effects strong sealing along the commissure line 16. This lip 18 approaches the size and shape of the natural commissure line of human heart valve. Tear strength of the lip 18 is equivalent of that of a film 10 times the thickness of any one leaflet. The combination of this heavy lip and leaflet provides for unusually reliable longevity since the ease of flexing depends upon the gossimer nature of the leaflet and the resistance to fatigue and tear upon the strength of the leading edge, i.e. the lip 18.

Provision is made to distribute any flexural stress at the base of the leaflets 14a, 14b and 14c where they join and frame by means of a smooth transitional area 20 of tapering thickness. Also, in conjunction with this transitional area 20 are radiating lines 22 consisting of heavier areas that give additional strength to the leaflets without adding to their overall bulk. These radiating reinforcement lines 22 serve also as built-in struts to aid in preventing prolapse of the leaflets and add dimensional stability over the extended periods of flexing.

The base 12' of the valve 10 serves as a suture ring which can be constructed from the same material as the rest of the frame or from a semi-rigid polyurethane foam as previously described. Cloth can be added for additional cushioning if desired. While the base 12' is preferably formed unitary with the struts 12a, 12b and 12c to form a one-piece frame 12 as shown, it will be understood that it can be formed as a separate flange piece and permanently bonded in place to the rest of the frame 12. The frame 12 which consists of the base ring section 12' and three struts 12a, 12b and 12c can be readily injection molded from Pellethane polyurethane (a polyether urethane) or the equivalent, under heat and pressure to form a uniform one-piece unit free from seams, joints, welds or other strain areas. A valuable adjunct to the injection molding of the frame is the incorporation of a vacuum chamber over the feeding hopper and hot-melt area of the machine. Much of the quality of the frame 12 is due to the total exclusion of small amounts of air which are usually trapped within injection molded parts. This arrangement excludes such inclusions and significantly increases the strength and fatigue resistance of the frame.

Subsequent annealing of the frame 12 is an important aspect of the fabrication scheme. Through this procedure, residual strains induced by the molding process are relieved, solvent resistance is significantly improved and heat distortion temperature is increased. A suitable set of conditions for this annealing is 200°–300° F. for 1 to more than 24 hours. In particular, 220°–260' F. for 12–20 hours or 240' F. for 16 hours, depending upon size of the frame, is suitable.

The three leaflets 14a, 14b and 14c which utlimately are attached to the frame 12, to make a one-piece unit 10, are formed in a series of steps. These steps consists of (1) forming a thin membrane by solvent casting techniques, (2) reinforcing the commissure area and radiating base lines by build-up discretely heavier areas, (3) drying the membrane and removing it from its former, (4) placing the so-formed membrane over a mandrel of metal (or any other rigid, heat resistant material) whose shape resembles that of the final leaflet design and (5) vacuum forming with heat and negative pressure to permanently establish the leaflet shape. These steps will be discussed seriatim.

(1) Forming a thin membrane by solvent casting

A dipping mandrel, such as a round ended glass tube, is carefully lowered into a solvent solution of the polyurethane and carefully withdrawn to preclude inclusion of entrapped air. Several dips may be required to achieve the appropriate thickness of polymer onto the glass. Prior to dipping, vacuum is used to remove all traces of air from the solution. Several solvents are suitable to achieve the optimum dipping viscosity such as dimethyl acetamide, tetrahydrafuran, dimethyl formamide, cyclohexanone, etc. A thin syrup-like consistency is best to provide enough body yet prevent the aforementioned inclusion of air. Once the appropriate thickness is achieved, the membrane is dried slowly in an air circulating oven to remove all traces of solvent.

The membrane can then be readily stripped from the glass and is ready for the next step of the sequence.

(2) Reinforcing the commissure area by building up a heavy edge of the membrane

Before removing the membrane from the mandrel, as previously described, the lip or leading edge of the so-formed leaflet is built-up with a heavier band of polyurethane. This band is intended to add strength and tear resistance to the membrane in the area of the commissure line. This can conveniently be done by providing the glass mandrel with a groove into which the polyurethane will accumulate excessively. The shape of the groove can vary from three symmetrically arranged loops to a simple circumferential one. Excess material from this lip can be precisely removed by cutting with a razor knife while the entire assembly is afixed in a machine lathe. The radiating lines 22 extending from the base of the leaflets are formed in the same manner.

(3) Drying the membrane and removing it from its former

It is essential that all solvent be removed from the membrane. This may be accomplished by drying overnight in a filtered air circulating oven at 50° C. Upon drying, the film can be readily peeled off the glass.

(4) Placing pre-formed membrane over a mandrel of metal whose shape resembles that of the final leaflet design and vacuum forming.

The pre-formed membrane is placed over a metal mandrel having the shape of the final construction. Vacuum and heat are applied, typically 15 psi for 5 minutes to one hour at 240–320° F. The hot assembly is allowed to cool to room temperature before the vacuum is cut off and the formed membrane removed.

The polyurethane frame 12 and the formed three leaflet membrane 14 are then joined as an integral unit in the following manner: The frame is oriented over a mandrel containing the shape of the tri-leaflet design (similar to that previously described). The pre-formed leaflet membrane is placed over the frame which has been treated with a coating of solvent (e.g. one of those solvents previously mentioned). This provides a bonding site in the area where the membrane overlaps the frame. An outer chamber of silicone rubber is used to cover the above assembly and provides a means of applying positive pressure to the bond line. This pressure is applied until the bond becomes permanent (typically about 5 minutes to one hour). The frame and its now intact membrane is removed from the assembly. The suture ring 12' if not formed unitary with the remainder of the frame, is applied to the frame's base. The final unit is dried in a filter air circulating oven at 50° C. overnight or until all solvent is removed.

The valve 10 is typically 0.55" high with a 0.86" inner diameter and 1.35" outer diameter (of the base ring 12'). The membrane 14 is suitably 4 to 10 mils thick with the commissure lip 18 being 8–30 mils thick and 20–80 mils wide.

Example

A tri-leaflet valve, constructed entirely of polyether urethane to optimize compatibility and strength, consists of a semi-rigid polyurethane framework 12 of 75 shore "D" durometer whose three projecting struts are continuous with and support of one-piece, highly flexible 0.15 mm membrane 14 of 80 shore "A" durometer which makes up the three leaflets of the valve. The leading edge of the leaflets forms the commissure and is reinforced with a narrow integral band of the same elastomer. Further reinforcement lines radiate from the frame/leaflet junction 20 to enhance durability without contributing appreciable bulk or stiffness. The highly gossimer leaflets require minimal operating force yet possess strength necessary at points of stress. Uniform stress distribution is effected by the flexibility of the valve frame which moves with the leaflets. The base 12' acts as a torsion bar to impart rigidity to the struts to prevent inversion.

Such valve 10 is formed using a two stage injection molding process from two polyurethanes of different hardnesses. Bond strengths at the interface approach that of the parent materials. Complex contours are achieved by machining and photoetching the stainless steel molds.

The valve obviates problems associated with previous tri-leaflet valves such as disruption of the union between frame and leaflets, premature leaflet failure and hydrolytic stability.

In vitro tests run on a modified pulse duplicator (Cornhill, J. F.: "An aortic-left ventricular pulse duplicator used in testing prosthetic aortic heart valves," *J. Thorac. & Cardio. Surg.* 73: 550–558, 1977) show performance to be near physiological over a wide range of heart rates, systolic/diastolic ratios, left ventricular and aortic pressures, flow rates, and fuid viscosity. Flow visualization using cinemaphotography shows complete closure and well oriented alignment along the commissure line with minimal regurgitation or stasis. Accelerated tests at twice the normal rate over a period of 14 days resulted in little or no change in dimensions and wear.

It will be obvious to those skilled in the art that various changes may be made without departing from the scope of the invention and the invention is not to be considered limited to what is shown in the drawing and described in the specification.

What is claimed is:

1. A method of producing an artificial heart valve, comprising the steps of:
    molding an artificial heart framework, including a base and struts, using polyurethane resin;
    forming an elastomeric membrane, of polyurethane resin which is thin relative to said framework, and forming a thickened commissure along the leading edge of said membrane, and forming a plurality of lines, thicker than said membrane, radiating from the base of said membrane;
    joining said framework with said elastomeric membrane using an adhesive cement, and permanently bonding said membrane to said framework.

2. A method according to claim 1, further comprising permanently bonding a suture ring to the base of said framework using solvent or adhesive cement.

3. A method of producing an artificial heart valve, comprising the steps of:
    injection molding a framework using polyurethane, including a base and struts of the heart valve;
    annealing said framework for relieving residual strains in said framework;
    forming an elastomeric membrane having a base and a commissure area, of polyurethane thin relative to said framework, by solvent casting, using a first mandrel, and reinforcing the commissure area by building up a lip, thick relative to the thickness of said membrane, along the leading edge of said membrane, and forming a plurality of lines, thicker than said membrane, radiating from the base of said membrane;
    drying said membrane to remove solvent therefrom;
    peeling said membrane from said first mandrel;
    orienting said framework over a second mandrel having a trileaflet design and coating said membrane with a polyurethane solvent;
    placing said membrane over said second mandrel, on said framework;
    applying solvent or adhesive cement, and pressure to a bond line between said membrane and said framework, until said membrane and framework are permanently bonded together;
    removing said framework and membrane from said second mandrel;
    permanently bonding a suture ring to the base of said framework using solvent or adhesive cement; and
    drying the valve to remove said solvent 4. A method, according to claim 3, wherein said membrane and the completed valve are dried at 50° C.

5. A method, according to claim 3, wherein the pressure applied to the boundary between said membrane and said framework is 15ps: for 5 minutes to one hour at between 240° and 320° F.

6. A method, according to claim 3, wherein said step of forming said elastomeric membrane by solvent casting comprises;
    forming a solution containing polyurethane and a solvent;
    removing all the air from said solution;
    dipping a first mandrel in said solution at least once;
    withdrawing said first mandrel from said solution so as to preclude trapping air in said solution.

7. A method, according to claim 3, further including;
    removing all the air from the injection molded parts before said framework is formed by injection molding.

8. A method, according to claim 3, wherein said annealing takes place at between 200° F. and 300° F. for between 1 and 24 hours.

9. A method, according to claim 6, wherein said solvent is dimethyl acetamide, tetrahydrofuran, dimethly formamide or cyclohexanone.

* * * * *